(12) United States Patent
Fukuoka et al.

(10) Patent No.: US 8,093,437 B2
(45) Date of Patent: Jan. 10, 2012

(54) INDUSTRIAL PROCESS FOR PRODUCTION OF DIOL

(75) Inventors: Shinsuke Fukuoka, Tokyo (JP); Hironori Miyaji, Tokyo (JP); Hiroshi Hachiya, Tokyo (JP); Kazuhiko Matsuzaki, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 710 days.

(21) Appl. No.: 11/991,419

(22) PCT Filed: Jan. 19, 2007

(86) PCT No.: PCT/JP2007/050810
§ 371 (c)(1),
(2), (4) Date: Sep. 25, 2008

(87) PCT Pub. No.: WO2007/086326
PCT Pub. Date: Aug. 2, 2007

(65) Prior Publication Data
US 2009/0018370 A1   Jan. 15, 2009

(30) Foreign Application Priority Data
Jan. 26, 2006   (JP) .................................. 2006-017520

(51) Int. Cl.
*C07C 31/18* (2006.01)
*B01J 19/00* (2006.01)
*B01D 3/00* (2006.01)

(52) U.S. Cl. ......................... 568/852; 422/211; 202/152

(58) Field of Classification Search .................. 568/852; 422/211; 202/152
See application file for complete search history.

(56) References Cited

U.S. PATENT DOCUMENTS

| 5,231,212 A | 7/1993 | Buysch et al. |
| 5,359,118 A | 10/1994 | Wagner et al. |
| 5,847,189 A | 12/1998 | Tojo et al. |
| 6,346,638 B1 | 2/2002 | Tojo et al. |
| 6,479,689 B1 | 11/2002 | Tojo et al. |

FOREIGN PATENT DOCUMENTS

| EP | 0530615 A2 | 8/1992 |
| EP | 0569812 A1 | 5/1993 |
| EP | 0889025 A1 | 1/1999 |
| EP | 1086940 A1 | 3/2001 |
| EP | 1174406 A1 | 1/2002 |
| JP | 04-198141 A | 7/1992 |
| JP | 04-230243 A | 8/1992 |
| JP | 5-213830 A | 8/1993 |
| JP | 6-9507 A | 1/1994 |
| JP | 8170086 A | 7/1996 |
| JP | 09-176061 A | 7/1997 |
| JP | 9-183744 A | 7/1997 |
| JP | 09-194435 A | 7/1997 |
| JP | 2002-308804 A | 10/2002 |
| JP | 2003-119168 A | 4/2003 |
| JP | 2003-300936 A | 10/2003 |
| JP | 2003-342209 A | 12/2003 |
| JP | 2004-131394 A | 4/2004 |
| WO | WO-97/23445 A1 | 7/1997 |
| WO | WO-99/64382 A1 | 12/1999 |
| WO | WO-00/51954 A1 | 9/2000 |
| WO | WO-03/006418 A1 | 1/2003 |
| WO | WO-2005/123638 A1 | 12/2005 |
| WO | WO-2006/030724 A1 | 3/2006 |

OTHER PUBLICATIONS

Supplementary European Search Report dated Oct. 5, 2009 for corresponding European Application No. 07707098.5.
European Official Communication dated Oct. 21, 2009 for Corresponding European Application No. 07707098.5.
Japan Petroleum Institute (ed.), "Sekiyu-kagaku Purosesu" ("Petrochemical Processes"), pp. 120-125, Kodansha, 2001.

*Primary Examiner* — Sikarl Witherspoon
(74) *Attorney, Agent, or Firm* — Birch, Stewart, Kolasch & Birch, LLP

(57) ABSTRACT

The invention provides an apparatus and process for producing a diol by taking a cyclic carbonate and an aliphatic monohydric alcohol as starting materials, continuously feeding the starting materials into column A, carrying out reactive distillation in column A, continuously withdrawing a low boiling point reaction mixture containing a produced dialkyl carbonate and the aliphatic monohydric alcohol from an upper portion of column A, continuously withdrawing a high boiling point reaction mixture containing a produced diol from a lower portion of column A, continuously feeding the high boiling point reaction mixture into distillation column C, distilling off material having a lower boiling point than that of the diol contained in the high boiling point reaction mixture as a column top component and a side cut component so as to obtain a column bottom component, continuously feeding the column bottom component into column C, and obtaining the diol.

30 Claims, 1 Drawing Sheet

INDUSTRIAL PROCESS FOR PRODUCTION OF DIOL

TECHNICAL FIELD

The present invention relates to a process for producing a diol industrially in a large amount stably for a prolonged period of time by continuously feeding a cyclic carbonate and an aliphatic monohydric alcohol into a reactive distillation column, carrying out a reactive distillation process, and obtaining a high boiling point reaction mixture having the diol as a main component thereof which is continuously withdrawn from the bottom of the reactive distillation column, and then continuously feeding the high boiling point reaction mixture into a continuous multi-stage distillation column for separating off material having a lower boiling point than that of the diol contained in the high boiling point reaction mixture, continuously obtaining the material having a lower boiling point than that of the diol as a column top component and a side cut component, and continuously obtaining the diol substantially not containing the material having a lower boiling point than that of the diol as a column bottom component.

BACKGROUND ART

A reactive distillation process for producing a dialkyl carbonate and a diol through reaction between a cyclic carbonate and an aliphatic monohydric alcohol has been first disclosed by the present inventors (see Patent Document 1: Japanese Patent Application Laid-Open No. 4-198141, Patent Document 2: Japanese Patent Application Laid-Open No. 4-230243, Patent Document 3: Japanese Patent Application Laid-Open No. 9-176061, Patent Document 4: Japanese Patent Application Laid-Open No. 9-183744, Patent Document 5: Japanese Patent Application Laid-Open No. 9-194435, Patent Document 6: International Publication No. WO97/23445 (corresponding to European Patent No. 0889025, and U.S. Pat. No. 5,847,189), Patent Document 7: International Publication No. WO99/64382 (corresponding to European Patent No. 1086940, and U.S. Pat. No. 6,346,638), Patent Document 8: International Publication No. WO00/51954 (corresponding to European Patent No. 1174406, and U.S. Pat. No. 6,479,689), Patent Document 9: Japanese Patent Application Laid-Open No. 2002-308804, Patent Document 10: Japanese Patent Application Laid-Open No. 2004-131394), and patent applications in which such a reactive distillation system is used have subsequently also been filed by other companies (see Patent Document 11: Japanese Patent Application Laid-Open No. 5-213830 (corresponding to European Patent No. 0530615, and U.S. Pat. No. 5,231,212), Patent Document 12: Japanese Patent Application Laid-Open No. 6-9507 (corresponding to European Patent No. 0569812, and U.S. Pat. No. 5,359,118), Patent Document 13: Japanese Patent Application Laid-Open No. 2003-119168 (corresponding to International Publication No. WO03/006418), Patent Document 14: Japanese Patent Application Laid-Open No. 2003-300936, Patent Document 15: Japanese Patent Application Laid-Open No. 2003-342209). In the case of using a reactive distillation system for this reaction, the reaction can be made to proceed with a high conversion. However, reactive distillation processes proposed hitherto have related to producing the dialkyl carbonate and the diol either in small amounts or for a short period of time, and have not related to carrying out the production on an industrial scale stably for a prolonged period of time. That is, these processes have not attained the object of producing a diol continuously in a large amount (e.g. not less than 1 ton/hr) stably for a prolonged period of time (e.g. not less than 1000 hours, preferably not less than 3000 hours, more preferably not less than 5000 hours).

For example, the maximum values of the height (H: cm), diameter (D: cm), and number of stages (n) of the reactive distillation column, the amount produced P (kg/hr) of ethylene glycol, and the continuous production time T (hr) in examples disclosed for the production of dimethyl carbonate (DMC) and ethylene glycol (EG) from ethylene carbonate and methanol are as in Table 1.

TABLE 1

| PATENT DOCUMENT | H:cm | D:cm | NO. STAGES:n | P:kg/hr | T:hr |
| --- | --- | --- | --- | --- | --- |
| 1 | 100 | 2 | 30 | 0.073 | 400 |
| 4 | 160 | 5 | 40 | 0.213 | NOTE 5 |
| 5 | 160 | 5 | 40 | 0.358 | NOTE 5 |
| 7 | 200 | 4 | PACKING COLUMN (Dixon) | 0.528 | NOTE 5 |
| 8 | NOTE 1 | 5 | 60 | 0.140 | NOTE 5 |
| 9 | NOTE 1 | 5 | 60 | 0.161 | NOTE 5 |
| 10 | NOTE 1 | 5 | 60 | 0.161 | NOTE 5 |
| 11 | 250 | 3 | PACKING COLUMN (Raschig) | 0.154 | NOTE 5 |
| 12 | NOTE 2 | NOTE 2 | NOTE 2 | 0.256 | NOTE 5 |
| 13 | NOTE 3 | NOTE 3 | 42 | NOTE 4 | NOTE 5 |
| 14 | NOTE 3 | NOTE 3 | 30 | 2490 | NOTE 5 |
| 15 | 200 | 15 | PACKING COLUMN (BX) | 19 | NOTE 5 |

NOTE 1 OLDERSHAW DISTILLATION COLUMN.
NOTE 2 NO DESCRIPTION WHATSOEVER DEFINING DISTILLATION COLUMN.
NOTE 3 ONLY DESCRIPTION DEFINING DISTILLATION COLUMN IS NUMBER OF STAGES.
NOTE 4 NO DESCRIPTION WHATSOEVER OF PRODUCED AMOUNT.
NOTE 5 NO DESCRIPTION WHATSOEVER REGARDING STABLE PRODUCTION FOR PROLONGED PERIOD OF TIME.

In Patent Document 14 (Japanese Patent Application Laid-Open No. 2003-300936), it is stated at paragraph 0060 "The present example uses the same process flow as for the preferred mode shown in FIG. 1 described above, and was carried out with the object of operating a commercial scale apparatus for producing dimethyl carbonate and ethylene glycol through transesterification by a catalytic conversion reaction between ethylene carbonate and methanol. Note that the following numerical values in the present example can be adequately used in the operation of an actual apparatus", and as that example it is stated that 2490 kg/hr of ethylene glycol was specifically produced. The scale described in that example corresponds to an annual production of 30,000 or more tons of dimethyl carbonate, and hence this implies that operation of the world's largest scale commercial plant using this process had been carried out at the time of the filing of the patent application for Patent Document 14 (Japanese Patent Application Laid-Open No. 2003-300936) (Apr. 9, 2002). However, even at the time of filing the present application, there is not the above fact at all. Moreover, in the example of Patent Document 14 (Japanese Patent Application Laid-Open No. 2003-300936), exactly the same value as the theoretically calculated value is stated for the amount of dimethyl carbonate produced, but the yield for ethylene glycol is approximately 85.6%, and the selectivity is approximately 88.4%, and hence it cannot really be said that a high yield and high selectivity have been attained. In particular, the low selectivity indicates that this process has a fatal drawback as an industrial production process. (Note also that Patent Document 14 (Japanese Patent Application Laid-Open No. 2003-300936) was deemed to have been withdrawn on Jul. 26, 2005 due to examination not having been requested).

With such a reactive distillation process, there are very many causes of fluctuation such as composition variation due to reaction and composition variation due to distillation in the distillation column, and temperature variation and pressure variation in the column, and hence continuing stable operation for a prolonged period of time is often accompanied by difficulties, and in particular these difficulties are further increased in the case of handling large amounts. To continue mass production of a dialkyl carbonate and a diol using a reactive distillation process stably for a prolonged period of time while maintaining high yield and high selectivity, and thus produce a diol, the process must be cleverly devised. However, the only description of continuous stable production for a prolonged period of time with a reactive distillation process proposed hitherto has been the 200 to 400 hours in Patent Document 1 (Japanese Patent Application Laid-Open No. 4-198141) and Patent Document 2 (Japanese Patent Application Laid-Open No. 4-230243).

The present inventors have proposed an industrial reactive distillation process that enables a dialkyl carbonate and a diol to be mass-produced continuously and stably for a prolonged period of time with high yield and high selectivity, but in addition to this, a process enabling a diol to be separated out and purified in a large amount stably for a prolonged period of time from a high boiling point reaction mixture continuously withdrawn in a large amount from a lower portion of the distillation column is also required, a process for producing a large amount of a diol with a high yield having been called for. The present invention has been devised to attain this object.

As shown in Table 1, with the exception of Patent Document 14 (Japanese Patent Application Laid-Open No. 2003-300936), the amount of the diol produced per hour using reactive distillation processes proposed hitherto has been a small amount. Moreover, with the process of Patent Document 14 (Japanese Patent Application Laid-Open No. 2003-300936), it is stated that approximately 2490 kg/hr of ethylene glycol containing approximately 130 kg/hr of unreacted ethylene carbonate and approximately 226 kg/hr of dihydroxyethyl carbonate was obtained as a column bottom component from a fourth step distillation column. However, this is merely a statement of the composition of the reaction mixture, there being no description whatsoever of production of a diol.

As a process for producing a diol of relatively high purity using reactive distillation and a diol purifying column, a process is known in which the diol is obtained from a side cut of the diol purifying column. For example, in the example (FIG. 5) in Patent Document 12 (Japanese Patent Application Laid-Open No. 6-9507 (corresponding to European Patent No. 0569812, and U.S. Pat. No. 5,359,118)), a high boiling point reaction mixture withdrawn from a lower portion of a reactive distillation column is fed into a thin film evaporator (III), high boiling point material obtained therefrom is fed into a thin film evaporator (IV), low boiling point evaporated material obtained therefrom is fed into a distillation column (VII), and ethylene glycol is obtained as a side cut component 22 from a concentrating portion of the distillation column (VII), and then purification is further carried out using a purifier (IX), whereby ethylene glycol is produced in an amount of 255 g/hr. That is, in the process of Patent Document 12 (Japanese Patent Application Laid-Open No. 6-9507 (corresponding to European Patent No. 0569812, and U.S. Pat. No. 5,359,118)), ethylene glycol is not obtained from the high boiling point reaction mixture until four purifying apparatuses have been used. Furthermore, the process of Patent Document 12 (Japanese Patent Application Laid-Open No. 6-9507 (corresponding to European Patent No. 0569812, and U.S. Pat. No. 5,359,118)) is a process in which a small amount of ethylene glycol is produced, there being no suggestions whatsoever regarding a process for producing a large amount (e.g. not less than 1 ton/hr) of a diol stably for a prolonged period of time (e.g. not less than 5000 hours).

Moreover, in, for example, example 1 (FIG. 5) in Patent Document 15 (Japanese Patent Application Laid-Open No. 2003-342209), a high boiling point reaction mixture withdrawn from a lower portion of a reactive distillation column is fed into a second distillation column 4, high boiling point material obtained therefrom is fed into a hydrolysis reactor 7, the reaction mixture therefrom is fed into a decarboxylation tank (gas-liquid separator 8), a liquid component obtained therefrom is fed into a third distillation column 10, and ethylene glycol is produced in an amount of 19 kg/hr as a side cut component from a stripping section of the third distillation column 10. However, with the process of Patent Document 15 (Japanese Patent Application Laid-Open No. 2003-342209), the ethylene glycol obtained contains 0.2% by weight of diethylene glycol. To obtain ethylene glycol as required as a starting material for a PET fiber or a PET resin using the process of Patent Document 15 (Japanese Patent Application Laid-Open No. 2003-342209), at least one further purifying apparatus is thus required. That is, with the process of Patent Document 15 (Japanese Patent Application Laid-Open No. 2003-342209), ethylene glycol is obtained from a side cut outlet installed in the stripping section, which is below an inlet for feeding into the distillation column, but the purity of the ethylene glycol is insufficient, and moreover the process of Patent Document 15 (Japanese Patent Application Laid-Open No. 2003-342209) is a process in which a small amount of ethylene glycol is produced, there being no suggestions whatsoever regarding a process for producing a large amount (e.g. not less than 1 ton/hr) of a diol stably for a prolonged period of time (e.g. not less than 5000 hours).

Moreover, in, for example, example 10 (FIG. 6) in Patent Document 8 (International Publication No. WO00/51954 (corresponding to European Patent No. 1174406, and U.S. Pat. No. 6,479,689)) and example 1 (FIG. 1) in Patent Document 9 (Japanese Patent Application Laid-Open No. 2002-308804), ethylene glycol is obtained from a side cut outlet installed in an enrichment section of an EG purifying column 41, which is above an inlet for feeding into the column, but in each case the amount produced is a small amount of less than 200 g/hr, there being no suggestions whatsoever regarding a process for producing a large amount (e.g. not less than 1 ton/hr) of a diol stably for a prolonged period of time (e.g. not less than 5000 hours).

Approximately 16 million tons per year (2004) of ethylene glycol is produced worldwide, but hitherto all of this has been through a hydration method in which water is added to ethylene oxide. However, as shown by the statement "Production of EG (ethylene glycol) is by a hydration reaction of EO (ethylene oxide), the reaction generally being carried out . . . at 150 to 200° C. At this time, not only is the target substance MEG (monoethylene glycol) produced, but moreover DEG (diethylene glycol) and TEG (triethylene glycol) are also by-produced. The proportions of these products depend on the water/EO ratio, and to obtain MEG with a selectivity of approximately 90%, the water/EO ratio must be made to be approximately 20 as a molar ratio. A large amount of water must thus be distilled off in an EG purification step, and a large amount of thermal energy is consumed in this . . . . With regard to synthesis of EG from EO, it is not an overstatement to say that this is an imperfect process from the viewpoint of energy efficiency." in Non-Patent Document 1 (Japan Petroleum Institute (ed.), "Sekiyu-kagaku Purosesu" ("Petrochemical Processes"), pages 120 to 125, Kodansha, 2001), this industrial production process has great drawbacks both from the perspective of the ethylene glycol yield and selectivity, and the perspective of energy saving.

DISCLOSURE OF INVENTION

Problems to be Solved by the Invention

It is an object of the present invention to provide a specific apparatus and process for producing a diol by taking a cyclic carbonate and an aliphatic monohydric alcohol as starting materials, continuously feeding the starting materials into a continuous multi-stage distillation column A in which a catalyst is present, carrying out reactive distillation in the column A, continuously withdrawing a low boiling point reaction mixture $A_T$ containing a produced dialkyl carbonate and the aliphatic monohydric alcohol from an upper portion of the column A in a gaseous form, continuously withdrawing a high boiling point reaction mixture $A_B$ containing a produced diol from a lower portion of the column A in a liquid form, then continuously feeding the high boiling point reaction mixture $A_B$ into a continuous multi-stage distillation column C for separating off material having a lower boiling point than that of the diol contained in the high boiling point reaction mixture $A_B$, continuously obtaining the material having a lower boiling point than that of the diol as a column top component $C_T$ and/or a side cut component $C_S$, and continuously obtaining the diol substantially not containing the material having a lower boiling point than that of the diol as a column bottom component $C_B$. Moreover, it is an object to thus provide a specific industrial apparatus and industrial production process that are inexpensive and, for example, enable the diol to be produced in an amount of not less than 1 ton/hr stably for a prolonged period of time (e.g. not less than 1000 hours, preferably not less than 3000 hours, more preferably not less than 5000 hours).

Means for Solving the Problems

That is, according to the first aspect of the present invention, there are provided:
1. in an industrial process for the production of a diol in which a diol is produced by taking a cyclic carbonate and an aliphatic monohydric alcohol as starting materials, continuously feeding the starting materials into a continuous multi-stage distillation column A in which a catalyst is present, carrying out reactive distillation in said column A, continuously withdrawing a low boiling point reaction mixture $A_T$ containing a produced dialkyl carbonate and said aliphatic monohydric alcohol from an upper portion of the column A in a gaseous form, continuously withdrawing a high boiling point reaction mixture $A_B$ containing a produced diol from a lower portion of the column A in a liquid form, then continuously feeding said high boiling point reaction mixture $A_B$ into a continuous multi-stage distillation column C for separating off material having a lower boiling point than that of the diol contained in said high boiling point reaction mixture $A_B$, continuously obtaining the material having a lower boiling point than the diol as a column top component $C_T$ and a side cut component $C_S$, and continuously obtaining the diol substantially not containing the material having a lower boiling point than that of the diol as a column bottom component $C_B$, wherein the improvement comprises:

(a) said continuous multi-stage distillation column C comprises a continuous multi-stage distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1$, $D_1$, $n_1$, $L_2$, $D_2$, and $n_2$ satisfy the following formulae (1) to (9):

$$300 \leq L_1 \leq 3000 \tag{1}$$

$$50 \leq D_1 \leq 700 \tag{2}$$

$$3 \leq L_1/D_1 \leq 30 \tag{3}$$

$$3 \leq n_1 \leq 30 \tag{4}$$

$$1000 \leq L_2 \leq 5000 \tag{5}$$

$$50 \leq D_2 \leq 500 \tag{6}$$

$$10 \leq L_2/D_2 \leq 50 \tag{7}$$

$$20 \leq n_2 \leq 100 \tag{8} \text{ and}$$

$$D_2 \leq D_1 \tag{9};$$

(b) the enrichment section of said continuous multi-stage distillation column C has at least one chimney tray installed therein as an internal, said chimney tray having installed therein one or more chimneys each having an opening having a cross-sectional area S (cm$^2$) satisfying the formula (10):

$$200 \leq S \leq 1000 \tag{10},$$

and each of the chimneys being such that a height h (cm) from said opening of said chimney to a gas outlet of said chimney satisfies the formula (11):

$$10 \leq h \leq 80 \tag{11}; \text{ and}$$

(c) a side cut outlet is connected to a liquid collecting portion of said chimney tray of said continuous multi-stage distillation column C,
2. the process according to item 1, wherein an amount produced of the diol is not less than 1 ton/hr,
3. the process according to item 1 or 2, wherein a plurality ($n_3$ stages) of trays K are further provided in a lower portion of the internals in a lowermost portion of the stripping section which is in a lower portion of said continuous multi-stage distillation column C, a liquid is continuously withdrawn from an uppermost stage of said trays K, and after heat is given to require for distillation in a reboiler, the heated liquid is returned into the distillation column C from a feeding port provided between the uppermost stage of the trays K and the internal in the lowermost portion of the stripping section, while a remainder of the liquid is fed into a lower tray in order, 4. the process according to item 3, wherein each of the trays K is a baffle tray, 5. the process according to item 3 or 4, wherein an inside diameter $D_3$ of said continuous multi-stage distillation column C where the trays K are present satisfies $D_1 \leq D_3$, 6. the process according to any one of items 3 to 5, wherein $L_1$, $D_1$, $L_1/D_1$, $n_1$, $L_2$, $D_2$, $L_2/D_2$, $n_2$, and $n_3$ for said continuous multi-stage distillation column C satisfy respectively $500 \leq L_1 \leq 2000$, $70 \leq D_1 \leq 500$, $5 \leq L_1/D_1 \leq 20$, $5 \leq n_1 \leq 20$, $1500 \leq L_2 \leq 4000$, $70 \leq D_2 \leq 400$, $15 \leq L_2/D_2 \leq 40$, $30 \leq n_2 \leq 90$, and $3 \leq n_3 \leq 20$, 7. the process according to any one of items 1 to 6, wherein the internal in the stripping section of said continuous multi-stage distillation column C and the internal excluding the chimney tray in the enrichment section are trays and/or packings, 8. the process according to item 7, wherein the internal in the stripping section of said continuous multi-stage distillation column C is the tray, and the internal excluding the chimney tray in the enrichment section are trays and/or structured packings, 9. the process according to item 7 or 8, wherein said tray is a sieve tray, 10. the process according to item 9, wherein said sieve tray has 100 to 1000 holes/m$^2$ in a sieve portion thereof, and a cross-sectional area per hole in a range of from 0.5 to 5 cm$^2$, 11. the process according to item 9 or 10, wherein an aperture ratio (a ratio of a total cross-sectional area of the hole in one tray stage to an area of the tray) of said sieve tray in the enrichment section of said continuous multi-stage distillation column C is in a range of from 2 to 15%, 12. the process according to any one of items 9 to 11, wherein an aperture ratio (a ratio of a total cross-sectional area of the hole in one tray stage to an area of the tray) of said sieve tray in the enrichment section of said continuous multi-stage distillation column C is in a range of from 1.5 to 12%, 13. the process according to any one of items 1 to 12, wherein an aperture ratio (a ratio of a total cross-sectional area of the opening in the chimney to an area of the chimney tray including a total cross-sectional area of the opening) of said chimney tray is in a range of from 10 to 40%, 14. the process according to any one of items 1 to 13, wherein said continuous multi-stage distillation column C has a column bottom temperature in a range of from 150 to 250° C., 15. the process according to any one of items 1 to 14, wherein said continuous multi-stage distillation column C has a column top pressure in a range of from 50000 to 300000 Pa, 16. the process according to any one of items 1 to 15, wherein said continuous multi-stage distillation column C has a reflux ratio in a range of from 0.3 to 5, 17. the process according to any one of items 1 to 16, wherein a content of the diol in said column top component $C_T$ is not more than 100 ppm, 18. the process according to any one of items 1 to 17, wherein a content of the diol in said side cut component $C_S$ is not more than 0.5% of the diol fed into said continuous multi-stage distillation column C.

In addition, according to the second aspect of the present invention, there are provided:

19. a continuous multi-stage distillation column being a continuous multi-stage distillation column C for producing a diol by taking a cyclic carbonate and an aliphatic monohydric alcohol as starting materials, continuously feeding the starting materials into a continuous multi-stage distillation column A in which a catalyst is present, carrying out reactive distillation in said column A, continuously withdrawing a low boiling point reaction mixture $A_T$ containing a produced dialkyl carbonate and the aliphatic monohydric alcohol from an upper portion of the column A in a gaseous form, continuously withdrawing a high boiling point reaction mixture $A_B$ containing a produced diol from a lower portion of the column A in a liquid form, then continuously feeding said high boiling point reaction mixture $A_B$ into a continuous multi-stage distillation column C for separating off material having a lower boiling point than that of the diol contained in said high boiling point reaction mixture $A_B$, continuously obtaining the material having a lower boiling point than that of the diol as a column top component $C_T$ and a side cut component $C_S$, and continuously obtaining the diol substantially not containing the material having a lower boiling point than that of the diol as a column bottom component $C_B$, wherein the improvement comprises:

(a) said continuous multi-stage distillation column C comprises a distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1$, $D_1$, $n_1$, $L_2$, $D_2$, and $n_2$ satisfy the following formulae (1) to (9):

$$300 \leq L_1 \leq 3000 \tag{1}$$

$$50 \leq D_1 \leq 700 \tag{2}$$

$$3 \leq L_1/D_1 \leq 30 \tag{3}$$

$$3 \leq n_1 \leq 30 \tag{4}$$

$$1000 \leq L_2 \leq 5000 \tag{5}$$

$$50 \leq D_2 \leq 500 \tag{6}$$

$$10 \leq L_2/D_2 \leq 50 \tag{7}$$

$$20 \leq n_2 \leq 100 \tag{8}$$

and $$D_2 \leq D_1 \tag{9};$$

(b) the enrichment section of said continuous multi-stage distillation column C has at least one chimney tray installed therein as an internal, the chimney tray having installed therein one or more chimneys each having an opening having a cross-sectional area S (cm$^2$) satisfying the formula (10):

$$200 \leq S \leq 1000 \tag{10},$$

and each of the chimneys being such that a height h (cm) from said opening of said chimney to a gas outlet of the chimney satisfies the formula (11):

$$10 \leq h \leq 80 \tag{11}; and$$

(c) a side cut outlet is connected to a liquid collecting portion of said chimney tray of said continuous multi-stage distillation column C, 20. the continuous multi-stage distillation column according to item 19, wherein a plurality ($n_3$ stages) of trays K are further provided in a lower portion of the internals in a lowermost portion of the stripping section which is in a lower portion of said continuous multi-stage distillation column C, a liquid is continuously withdrawn from an uppermost stage of the trays K, and after heat is given to require for distillation in a reboiler, the heated liquid is returned into the distillation column C from a feeding port provided between the uppermost stage of the trays K and the internal in the lowermost portion of the stripping section, while a remainder of the liquid is fed into a lower tray in order.

21. the continuous multi-stage distillation column according to item 20, wherein each of the trays K is a baffle tray,
22. the continuous multi-stage distillation column according to item 20 or 21, wherein an inside diameter $D_3$ of said column where the trays K are present satisfies $D_1 \leq D_3$,
23. the continuous multi-stage distillation column according to any one of items 19 to 22, wherein $L_1, D_1, L_1/D_1, n_1, L_2, D_2, L_2/D_2, n_2$, and $n_3$ satisfy respectively $500 \leq L_1 \leq 2000$, $70 \leq D_1 \leq 500$, $5 \leq L_1/D_1 \leq 20$, $5 \leq n_1 \leq 20$, $1500 \leq L_2 \leq 4000$, $70 \leq D_2 \leq 400$, $15 \leq L_2/D_2 \leq 40$, $30 \leq n_2 \leq 90$, and $3 \leq n_3 \leq 20$,
24. the continuous multi-stage distillation column according to any of items 19 to 23, wherein the internal in the stripping section of the stripping section and the internal excluding the chimney tray in the enrichment section are trays and/or packings,
25. the continuous multi-stage distillation column according to item 24, wherein the internal in the stripping section is a tray, and the internal excluding the chimney tray in the enrichment section is a tray and/or a structured packing,
26. the continuous multi-stage distillation column according to item 24 or 25, wherein said tray is a sieve tray,
27. the continuous multi-stage distillation column according to item 26, wherein said sieve tray has 100 to 1000 holes/m² in a sieve portion thereof, and a cross-sectional area per hole in a range of from 0.5 to 5 cm²,
28. the continuous multi-stage distillation column according to item 26 or 27, wherein an aperture ratio (a ratio of a total cross-sectional area of the hole in one tray stage to an area of the tray) of said sieve tray in the stripping section is in a range of from 2 to 15%,
29. the continuous multi-stage distillation column according to any one of items 26 to 28, wherein an aperture ratio (a ratio of a total cross-sectional area of the hole in one tray stage to an area of the tray) of said sieve trays in the enrichment section is in a range of from 1.5 to 12%,
30. the continuous multi-stage distillation column according to any one of items 19 to 29, wherein an aperture ratio (a ratio of a total cross-sectional area of the opening in the chimneys to an area of the chimney tray including a total cross-sectional area of the opening) of said chimney tray is in a range of from 10 to 40%.

Advantageous Effects of Invention

According to the specific apparatus and process provided by the present invention, there are provided an industrial apparatus and industrial production process that are inexpensive and enable a diol substantially not containing material having a lower boiling point than that of the diol to be produced, from a cyclic carbonate and an aliphatic monohydric alcohol, with a high yield (e.g. generally not less than 97%, preferably not less than 98%, more preferably not less than 99%, based on the cyclic carbonate used) on an industrial scale of not less than 1 ton/hr, preferably not less than 2 tons/hr, more preferably not less than 3 tons/hr stably for a prolonged period of time of, for example, not less than 1000 hours, preferably not less than 3000 hours, more preferably not less than 5000 hours.

Moreover, the process according to the present invention differs from an existing ethylene glycol production process in that ethylene glycol can be produced by the process according to the present invention with a high yield and a high selectivity without using a large amount of water, and thus achieves excellent effects as an industrial production process that simultaneously solves two long-standing problems with the existing industrial production process (low selectivity, high energy use).

DESCRIPTION OF REFERENCE NUMERALS

Figure 1:
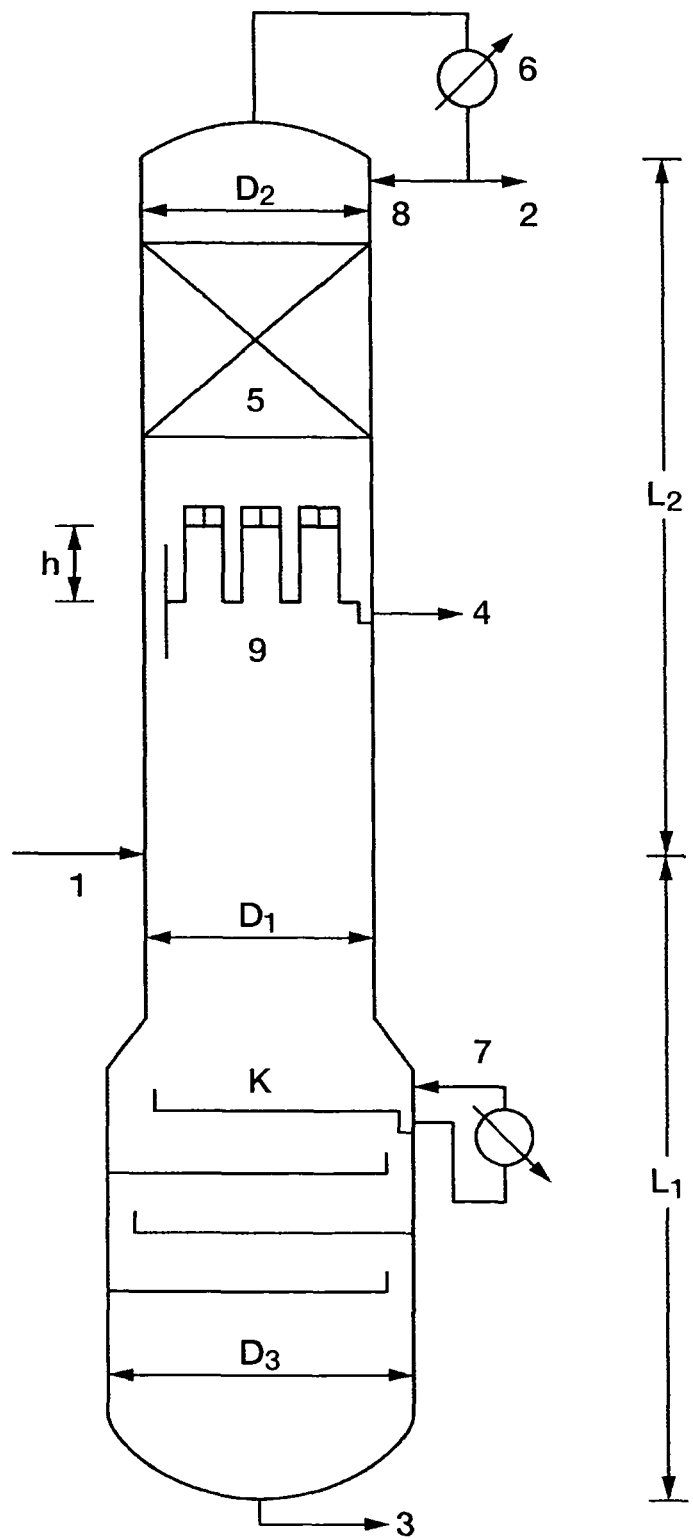
FIG. 1 is a schematic view showing an example of a continuous multi-stage distillation column C preferable for carrying out the present invention, $n_1$ stages of trays being installed in a stripping section, and trays being installed in a lower portion and structured packings in an upper portion (total number of stages $n_2$) in an enrichment section, as an internal in a trunk portion of the column, and one chimney tray stage being installed in the concentrating portion above an inlet 1 (Note that in FIG. 1, the trays excluding the chimney tray in the stripping section and the enrichment section are omitted), and a diameter $D_3$ of the lower portion of the column is greater than a diameter $D_1$ of the enrichment section, trays K ($n_3$ stages) being provided therein.

1: inlet, 2: outlet of column top component $C_T$, 3: outlet of column bottom component $C_B$, 4: outlet of side cut component $C_S$, 5: internal (packing), 6: heat exchanger, 7: reboiler, 8: inlet of reflux liquid, 9: chimney tray, h: height (cm) from an opening of chimney to a gas outlet of chimney, $L_1$: length (cm) of stripping section of continuous multi-stage distillation column C, $L_2$: length (cm) of enrichment section of continuous multi-stage distillation column C, $D_1$: inside diameter (cm) of stripping section of continuous multi-stage distillation column C, $D_2$: inside diameter (cm) of enrichment section of continuous multi-stage distillation column C, K: tray.

BEST MODE FOR CARRYING OUT THE INVENTION

Following is a detailed description of the present invention.
The reaction of the present invention is a reversible equilibrium transesterification reaction represented by the following formula in which a dialkyl carbonate and a diol are produced from a cyclic carbonate and an aliphatic monohydric alcohol:

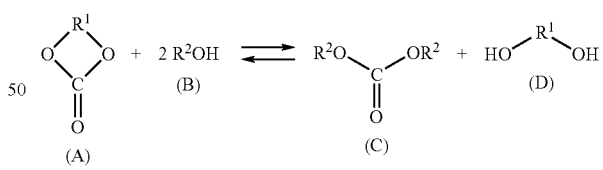

wherein $R^1$ represents a bivalent group $-(CH_2)_m-$ (m is an integer from 2 to 6), one or more of the hydrogens thereof being optionally substituted with an alkyl group or aryl group having 1 to 10 carbon atoms. Moreover, $R^2$ represents a monovalent aliphatic group having 1 to 12 carbon atoms, one or more of the hydrogens thereof being optionally substituted with an alkyl group or aryl group having 1 to 10 carbon atoms.

The cyclic carbonate used as a starting material in the present invention is a compound represented by (A) in the above formula. For example, an alkylene carbonate such as ethylene carbonate or propylene carbonate, or 1,3-dioxacyclohexa-2-one, 1,3-dioxacyclohepta-2-one, or the like can be preferably used, ethylene carbonate or propylene carbonate being more preferably used due to ease of procurement and so on, and ethylene carbonate being particularly preferably used.

Moreover, the aliphatic monohydric alcohol used as the other starting material is a compound represented by (B) in the above formula, one having a lower boiling point than that of the diol produced being used. Although possibly varying depending on the type of the cyclic carbonate used, examples of the aliphatic monohydric alcohol include methanol, ethanol, propanol (isomers), allyl alcohol, butanol (isomers), 3-buten-1-ol, amyl alcohol (isomers), hexyl alcohol (isomers), heptyl alcohol (isomers), octyl alcohol (isomers), nonyl alcohol (isomers), decyl alcohol (isomers), undecyl alcohol (isomers), dodecyl alcohol (isomers), cyclopentanol, cyclohexanol, cycloheptanol, cyclooctanol, methylcyclopentanol (isomers), ethylcyclopentanol (isomers), methylcyclohexanol (isomers), ethylcyclohexanol (isomers), dimethylcyclohexanol (isomers), methylcyclohexanol (isomers), phenylcyclohexanol (isomers), benzyl alcohol, phenethyl alcohol (isomers), phenylpropanol (isomers), and so on. Furthermore, these aliphatic monohydric alcohols may be substituted with substituents such as halogens, lower alkoxy groups, cyano groups, alkoxycarbonyl groups, aryloxycarbonyl groups, acyloxy groups, and nitro groups.

Of such aliphatic monohydric alcohols, ones preferably used are alcohols having 1 to 6 carbon atoms, more preferably alcohols having 1 to 4 carbon atoms, i.e. methanol, ethanol, propanol (isomers), and butanol (isomers). In the case of using ethylene carbonate or propylene carbonate as the cyclic carbonate, preferable aliphatic monohydric alcohols are methanol and ethanol, methanol being particularly preferable.

In the process of the present invention, a catalyst is made to be present in a reactive distillation column A. The method of making the catalyst be present in the reactive distillation column A may be any method, but in the case, for example, of a homogeneous catalyst that dissolves in the reaction liquid under the reaction conditions, the catalyst can be made to be present in a liquid phase in the reactive distillation column by feeding the catalyst into the reactive distillation column continuously, or in the case of a heterogeneous catalyst that does not dissolve in the reaction liquid under the reaction conditions, the catalyst can be made to be present in the reaction system by disposing the catalyst as a solid in the reactive distillation column; these methods may also be used in combination.

In the case that a homogeneous catalyst is continuously fed into the reactive distillation column, the homogeneous catalyst may be fed in together with the cyclic carbonate and/or the aliphatic monohydric alcohol, or may be fed in at a different position to the starting materials. The reaction actually proceeds in the distillation column in a region below the position at which the catalyst is fed in, and hence it is preferable to feed the catalyst into a region between the top of the column and the position(s) at which the starting materials are fed in. The catalyst must be present in at least 5 stages, preferably at least 7 stages, more preferably at least 10 stages.

Moreover, in the case of using a heterogeneous solid catalyst, the catalyst must be present in at least 5 stages, preferably at least 7 stages, more preferably at least 10 stages. A solid catalyst that also has an effect as a packing in the distillation column may also be used.

As the catalyst used in the present invention, any of various catalysts known from hitherto can be used. Examples of the catalyst include:

alkali metals and alkaline earth metals such as lithium, sodium, potassium, rubidium, cesium, magnesium, calcium, strontium, and barium;

basic compounds of alkali metals and alkaline earth metals such as hydrides, hydroxides, alkoxides, aryloxides, and amides;

basic compounds of alkali metals and alkaline earth metals such as carbonates, bicarbonates, and organic acid salts;

tertiary amines such as triethylamine, tributylamine, trihexylamine, and benzyldiethylamine;

nitrogen-containing heteroaromatic compounds such as N-alkylpyrroles, N-alkylindoles, oxazoles, N-alkylimidazoles, N-alkylpyrazoles, oxadiazoles, pyridine, alkylpyridines, quinoline, alkylquinolines, isoquinoline, alkylisoquinolines, acridine, alkylacridines, phenanthroline, alkylphenanthrolines, pyrimidine, alkylpyrimidines, pyrazine, alkylpyrazines, triazines, and alkyltriazines;

cyclic amidines such as diazobicycloundecene (DBU) and diazobicyclononene (DBN);

thallium compounds such as thallium oxide, thallium halides, thallium hydroxide, thallium carbonate, thallium nitrate, thallium sulfate, and thallium organic acid salts;

tin compounds such as tributylmethoxytin, tributylethoxytin, dibutyldimethoxytin, diethyldiethoxytin, dibutyldiethoxytin, dibutylphenoxytin, diphenylmethoxytin, dibutyltin acetate, tributyltin chloride, and tin 2-ethylhexanoate;

zinc compounds such as dimethoxyzinc, diethoxyzinc, ethylenedioxyzinc, and dibutoxyzinc;

aluminum compounds such as aluminum trimethoxide, aluminum triisopropoxide, and aluminum tributoxide;

titanium compounds such as tetramethoxytitanium, tetraethoxytitanium, tetrabutoxytitanium, dichlorodimethoxytitanium, tetraisopropoxytitanium, titanium acetate, and titanium acetylacetonate;

phosphorus compounds such as trimethylphosphine, triethylphosphine, tributylphosphine, triphenylphosphine, tributylmethylphosphonium halides, trioctylbutylphosphonium halides, and triphenylmethylphosphonium halides;

zirconium compounds such as zirconium halides, zirconium acetylacetonate, zirconium alkoxides, and zirconium acetate;

lead and lead-containing compounds, for example lead oxides such as $PbO$, $PbO_2$, and $Pb_3O_4$;

lead sulfides such as $PbS$, $Pb_2S_3$, and $PbS_2$;

lead hydroxides such as $Pb(OH)_2$, $Pb_3O_2(OH)_2$, $Pb_2[PbO_2(OH)_2]$, and $Pb_2O(OH)_2$;

plumbites such as $Na_2PbO_2$, $K_2PbO_2$, $NaHPbO_2$, and $KHPbO_2$;

plumbates such as $Na_2PbO_3$, $Na_2H_2PbO_4$, $K_2PbO_3$, $K_2[Pb(OH)_6]$, $K_4PbO_4$, $Ca_2PbO_4$, and $CaPbO_3$;

lead carbonates and basic salts thereof such as $PbCO_3$ and $2PbCO_3 \cdot Pb(OH)_2$;

alkoxylead compounds and aryloxylead compounds such as $Pb(OCH_3)_2$, $(CH_3O)Pb(OPh)$, and $Pb(OPh)_2$;

lead salts of organic acids, and carbonates and basic salts thereof, such as $Pb(OCOCH_3)_2$, $Pb(OCOCH_3)_4$, and $Pb(OCOCH_3)_2 \cdot PbO \cdot 3H_2O$;

organolead compounds such as $Bu_4Pb$, $Ph_4Pb$, $Bu_3PbCl$, $Ph_3PbBr$, $Ph_3Pb$ (or $Ph_6Pb_2$), $Bu_3PbOH$, and $Ph_2PbO$ (wherein Bu represents a butyl group, and Ph represents a phenyl group);

lead alloys such as Pb—Na, Pb—Ca, Pb—Ba, Pb—Sn, and Pb—Sb;

lead minerals such as galena and zinc blende; and hydrates of such lead compounds.

In the case that the compound used dissolves in a starting material of the reaction, the reaction mixture, a reaction by-product or the like, the compound can be used as a homogeneous catalyst, whereas in the case that the compound does not dissolve, the compound can be used as a solid catalyst. Furthermore, it is also preferable to use, as a homogeneous catalyst, a mixture obtained by dissolving a compound as above in a starting material of the reaction, the reaction mixture, a reaction by-product or the like in advance, or by reacting to bring about dissolution.

Furthermore, ion exchangers such as anion exchange resins having tertiary amino groups, ion exchange resins having amide groups, ion exchange resins having at least one type of exchange groups selected from sulfonate groups, carboxylate groups and phosphate groups, and solid strongly basic anion exchangers having quaternary ammonium groups as exchange groups; solid inorganic compounds such as silica, silica-alumina, silica-magnesia, aluminosilicates, gallium silicate, various zeolites, various metal-exchanged zeolites, and ammonium-exchanged zeolites, and so on can also be used as a heterogeneous catalyst.

As a heterogeneous catalyst, a particularly preferably used one is a solid strongly basic anion exchanger having quaternary ammonium groups as exchange groups, examples thereof including a strongly basic anion exchange resin having quaternary ammonium groups as exchange groups, a cellulose strongly basic anion exchanger having quaternary ammonium groups as exchange groups, and an inorganic carrier supported type strongly basic anion exchanger having quaternary ammonium groups as exchange groups. As a strongly basic anion exchange resin having quaternary ammonium groups as exchange groups, for example a styrene type strongly basic anion exchange resin or the like can be preferably used. A styrene type strongly basic anion exchange resin is a strongly basic anion exchange resin having a copolymer of styrene and divinylbenzene as a parent material, and having quaternary ammonium groups (type I or type II) as exchange groups, and can be schematically represented, for example, by the following formula:

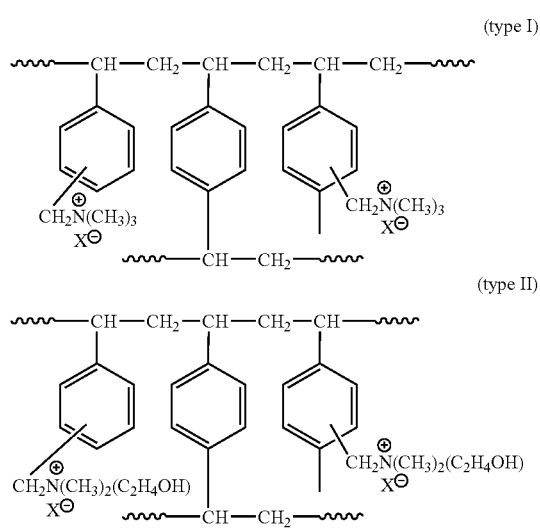

wherein X represents an anion; as X, generally at least one type of anion selected from $F^-$, $Cl^-$, $Br^-$, $I^-$, $HCO_3^-$, $CO_3^{2-}$, $CH_3CO_2^-$, $HCO_2^-$, $IO_3^-$, $BrO_3^-$, and $ClO_3^-$ is used, preferably at least one type of anion selected from $Cl^-$, $Br^-$, $HCO_3^-$, and $CO_3^{2-}$. Moreover, as the structure of the resin parent material, either a gel type one or a macroreticular (MR) type one can be used, the MR type being particularly preferable due to the organic solvent resistance being high.

An example of a cellulose strongly basic anion exchanger having quaternary ammonium groups as exchange groups is cellulose having $-OCH_2CH_2NR_3X$ exchange groups obtained by converting some or all of the $-OH$ groups in the cellulose into trialkylaminoethyl groups. Here, R represents an alkyl group; methyl, ethyl, propyl, butyl or the like is generally used, preferably methyl or ethyl. Moreover, X represents an anion as above.

An inorganic carrier supported type strongly basic anion exchanger having quaternary ammonium groups as exchange groups that can be used in the present invention means an inorganic carrier that has had $-O(CH_2)_nNR_3X$ quaternary ammonium groups introduced thereto by modifying some or all of the $-OH$ surface hydroxyl groups of the inorganic carrier. Here, R and X are defined as above. n is generally an integer from 1 to 6, preferably n=2. As the inorganic carrier, silica, alumina, silica-alumina, titania, a zeolite, or the like can be used, it being preferable to use silica, alumina, or silica-alumina, particularly preferably silica. Any method can be used as the method of modifying the surface hydroxyl groups of the inorganic carrier.

As the solid strongly basic anion exchanger having quaternary ammonium groups as exchange groups, a commercially available one may be used. In this case, the anion exchanger may also be used as the transesterification catalyst after being subjected to ion exchange with a desired anionic species in advance as pretreatment.

Moreover, a solid catalyst containing a macroreticular or gel-type organic polymer having bonded thereto heterocyclic groups each containing at least one nitrogen atom, or an inorganic carrier having bonded thereto heterocyclic groups each containing at least one nitrogen atom can also be preferably used as the transesterification catalyst. Furthermore, a solid catalyst in which some or all of these nitrogen-containing heterocyclic groups have been converted into a quaternary salt can be similarly used. Note that a solid catalyst such as an ion exchanger may also act as a packing in the present invention.

The amount of the catalyst used in the present invention varies depending on the type of the catalyst used, but in the case of continuously feeding in a homogeneous catalyst that dissolves in the reaction liquid under the reaction conditions, the amount used is generally in a range of from 0.0001 to 50% by weight, preferably from 0.005 to 20% by weight, more preferably from 0.01 to 10% by weight, as a proportion of the total weight of the cyclic carbonate and the aliphatic monohydric alcohol fed in as the starting materials. Moreover, in the case of using a solid catalyst installed in the distillation column, the catalyst is preferably used in an amount in a range of from 0.01 to 75 vol %, more preferably from 0.05 to 60 vol %, yet more preferably from 0.1 to 60 vol %, based on the empty column volume of the distillation column.

There are no particular limitations on the method of continuously feeding the cyclic carbonate and the aliphatic monohydric alcohol into the continuous multi-stage distillation column A constituting the reactive distillation column in the present invention; any feeding method may be used so long as the cyclic carbonate and the aliphatic monohydric alcohol can be made to contact the catalyst in a region of at least 5 stages, preferably at least 7 stages, more preferably at least 10 stages, of the distillation column A. That is, the cyclic carbonate and the aliphatic monohydric alcohol can be continuously fed in from a required number of inlets in stages of the continuous multi-stage distillation column A satisfying the conditions described earlier. Moreover, the cyclic carbonate and the aliphatic monohydric alcohol may be introduced into the same stage of the distillation column, or may be introduced into different stages to one another.

The starting materials may be fed continuously into the distillation column A in a liquid form, in a gaseous form, or as a mixture of a liquid and a gas. Other than feeding the starting materials into the distillation column A in this way, it is also preferable to additionally feed in a gaseous starting material intermittently or continuously from the lower portion of the distillation column A. Moreover, another preferable method is one in which the cyclic carbonate is continuously fed in a liquid form or a gas/liquid mixed form into a stage of the distillation column A above the stages in which the catalyst is present, and the aliphatic monohydric alcohol is continuously fed in a gaseous form and/or a liquid form into the lower portion of the distillation column A. In this case, the cyclic carbonate may of course contain the aliphatic monohydric alcohol.

In the present invention, the starting materials fed in may contain the product dialkyl carbonate and/or diol. The content thereof is, for the dialkyl carbonate, generally in a range of from 0 to 40% by weight, preferably from 0 to 30% by weight, more preferably from 0 to 20% by weight, in terms of the percentage by mass of the dialkyl carbonate in the aliphatic monohydric alcohol/dialkyl carbonate mixture, and is, for the diol, generally in a range of from 0 to 10% by weight, preferably 0 to 7% by weight, more preferably 0 to 5% by weight, in terms of the percentage by weight of the diol in the cyclic carbonate/diol mixture.

When carrying out the present reaction industrially, besides fresh cyclic carbonate and/or aliphatic monohydric alcohol newly introduced into the reaction system, material having the cyclic carbonate and/or the aliphatic monohydric alcohol as a main component thereof recovered from this process and/or another process can also be preferably used for the starting materials. It is an excellent characteristic feature of the present invention that this is possible. An example of another process is a process in which a diaryl carbonate is produced from the dialkyl carbonate and an aromatic monohydroxy compound, the aliphatic monohydric alcohol being by-produced in this process and recovered. The recovered by-produced aliphatic monohydric alcohol generally often contains the dialkyl carbonate, the aromatic monohydroxy compound, an alkyl aryl ether and so on, and may also contain small amounts of an alkyl aryl carbonate, the diaryl carbonate and so on. The by-produced aliphatic monohydric alcohol may be used as is as a starting material in the present invention, or may be used as a starting material after the amount of contained material having a higher boiling point than the aliphatic monohydric alcohol has been reduced through distillation or the like.

A cyclic carbonate preferably used in the present invention is one produced through reaction between, for example, an alkylene oxide such as ethylene oxide, propylene oxide or styrene oxide and carbon dioxide; a cyclic carbonate containing small amounts of such starting material compounds or the like may be used as a starting material in the present invention.

In the present invention, a ratio between the amounts of the cyclic carbonate and the aliphatic monohydric alcohol fed into the reactive distillation column A varies according to the type and amount of the transesterification catalyst and the reaction conditions, but a molar ratio of the aliphatic monohydric alcohol to the cyclic carbonate fed in is generally in a range of from 0.01 to 1000 times. To increase the cyclic carbonate conversion, it is preferable to feed in the aliphatic monohydric alcohol in an excess of at least 2 times the number of mols of the cyclic carbonate. However, if an amount of the aliphatic monohydric alcohol used is too great, then it is necessary to make the apparatus larger. For such reasons, a molar ratio of the aliphatic monohydric alcohol to the cyclic carbonate is preferably in a range of from 2 to 20, more preferably from 3 to 15, yet more preferably from 5 to 12. Furthermore, if much unreacted cyclic carbonate remains, then the unreacted cyclic carbonate may react with the product diol to by-produce oligomers such as a dimer or a trimer, and hence in the case of industrial implementation, it is preferable to reduce the amount of unreacted cyclic carbonate remaining as much as possible. In the process of the present invention, even if the above molar ratio is not more than 10, the cyclic carbonate conversion can be made to be not less than 98%, preferably not less than 99%, more preferably not less than 99.9%. This is another characteristic feature of the present invention.

In the present invention, preferably not less than approximately 1 ton/hr of a high boiling point reaction mixture $A_B$ containing the diol is continuously produced in the reactive distillation column A, this being fed into a continuous multi-stage distillation column C, so as to produce not less than approximately 1 ton/hr of the diol substantially not containing material having a lower boiling point than that of the diol as a column bottom component $C_B$; the minimum amount of the cyclic carbonate continuously fed in to achieve this is generally 1.55 P ton/hr, preferably 1.5 P ton/hr, more preferably 1.45 P ton/hr, based on the amount P (ton/hr) of the diol to be produced. In a yet more preferable case, this amount can be made to be less than 1.43 P ton/hr.

There are no particular limitations on the continuous multi-stage distillation column A for carrying out the reactive distillation process in the present invention, but the continuous multi-stage distillation column A is preferably one that enables not only distillation but also reaction to be carried out at the same time so as to be able to produce preferably not less than 1.5 ton/hr of the dialkyl carbonate and/or preferably not less than 1 ton/hr of the diol stably for a prolonged period of time.

In the present invention, the diol is produced by taking the cyclic carbonate and the aliphatic monohydric alcohol as starting materials, continuously feeding the starting materials into the continuous multi-stage distillation column A in which the catalyst is present, carrying out reactive distillation in the column A, continuously withdrawing a low boiling point reaction mixture $A_T$ containing a produced dialkyl carbonate and the aliphatic monohydric alcohol from an upper portion of the column A in a gaseous form, continuously withdrawing a high boiling point reaction mixture $A_B$ containing a produced diol from a lower portion of the column A in a liquid form, continuously feeding the high boiling point reaction mixture $A_B$ into a continuous multi-stage distillation column C, continuously obtaining material having a lower boiling point than that of the diol contained in the high boiling point reaction mixture $A_B$ as a column top component $C_T$ and/or a side cut component $C_S$, and continuously obtaining the diol substantially not containing the material having a lower boiling point than that of the diol. The continuous multi-stage distillation column C must thus have a function of enabling the material having a lower boiling point than that of the diol contained in the high boiling point reaction mixture $A_B$ to be removed efficiently as the column top component $C_T$ and/or the side cut component $C_S$; the present invention provides an industrial distillation apparatus having a specified structure having this function, and it has been discovered that by using this apparatus, the object of the present invention can be attained.

The high boiling point reaction mixture $A_B$ may contain a trace to a small amount of unreacted cyclic carbonate. In this case, it is preferable to make it such that such unreacted cyclic carbonate is substantially not present in the column bottom component $C_B$ from the continuous multi-stage distillation column C. To achieve this, it is preferable to add a small amount of water into the continuous multi-stage distillation column C so that the unreacted cyclic carbonate is converted into the diol through hydrolysis, and/or devise the continuous multi-stage distillation column C such that the unreacted cyclic carbonate is reacted with the diol and thus converted into a dialkylene glycol or the like (e.g. for a temperature and residence time required for this reaction to proceed to completion to be secured, for back mixing of the column bottom component to be reduced, etc.). As a result, it can be made to be such that there is substantially no unreacted cyclic carbonate in the column bottom component $C_B$ from the continuous multi-stage distillation column C, this being preferable when carrying out the present invention.

Note that the term "substantially not containing" used in the present invention means that the content is not more than 50 ppm, preferably not more than 10 ppm, more preferably not more than 5 ppm.

To attain the above object, the continuous multi-stage distillation column C used in the present invention must be made to simultaneously satisfy various conditions.

Specifically, the continuous multi-stage distillation column C must be as follows:

(a) the continuous multi-stage distillation column C comprises a distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1$, $D_1$, $n_1$, $L_2$, $D_2$, and $n_2$ satisfy the following formulae (1) to (9):

$$300 \leq L_1 \leq 3000 \quad (1)$$

$$50 \leq D_1 \leq 700 \quad (2)$$

$$3 \leq L_1/D_1 \leq 30 \quad (3)$$

$$3 \leq n_1 \leq 30 \quad (4)$$

$$1000 \leq L_2 \leq 5000 \quad (5)$$

$$50 \leq D_2 \leq 500 \quad (6)$$

$$10 \leq L_2/D_2 \leq 50 \quad (7)$$

$$20 \leq n_2 \leq 100 \quad (8) \text{ and}$$

$$D_2 \leq D_1 \quad (9);$$

(b) the enrichment section of the continuous multi-stage distillation column C has at least one chimney tray installed therein as the internal, the chimney tray having installed therein one or more chimneys each having an opening having a cross-sectional area S (cm$^2$) satisfying the formula (10):

$$200 \leq S \leq 1000 \quad (10),$$

and each of the chimneys being such that a height h (cm) from the opening of the chimney to a gas outlet of the chimney satisfies the formula (11):

$$10 \leq h \leq 80 \quad (11); \text{ and}$$

(c) a side cut outlet is connected to a liquid collecting portion of the chimney tray of the continuous multi-stage distillation column C.

It has been discovered that by using such a continuous multi-stage distillation column C, a column bottom component $C_B$ substantially not containing material having a lower boiling point than that of the diol can be produced on an industrial scale of not less than 1 ton/hr, preferably not less than 2 tons/hr, more preferably not less than 3 tons/hr, stably for a prolonged period of time of, for example, not less than 1000 hours, preferably not less than 3000 hours, more preferably not less than 5000 hours, from a large amount of the high boiling point reaction mixture $A_B$ which has been produced through a reactive distillation process between the cyclic carbonate and the aliphatic monohydric alcohol. The reason why it has become possible to separate out and purify the diol on an industrial scale with such excellent effects by implementing the process according to the present invention is not clear, but this is supposed to be due to a composite effect brought about when the conditions of the formulae (1) to (11) are combined.

Preferable ranges for the respective factors are described below.

If $L_1$ (cm) is less than 300, then the separation efficiency for the stripping section decreases, and hence the desired separation efficiency cannot be attained. Moreover, to keep down the equipment cost while securing the desired separation efficiency, $L_1$ must be made to be not more than 3000. Furthermore, if $L_1$ is greater than 3000, then the pressure difference between the top and bottom of the column becomes too great, and hence prolonged stable operation becomes difficult, and moreover it becomes necessary to increase the temperature in the lower portion of the column, and hence side reactions become liable to occur. A more preferable range for $L_1$ (cm) is $500 \leq L_1 \leq 2000$, with $600 \leq L_1 \leq 1500$ being yet more preferable.

If $D_1$ (cm) is less than 50, then it is not possible to attain the desired distillation amount. Moreover, to keep down the equipment cost while attaining the desired distillation amount, $D_1$ must be made to be not more than 700. A more preferable range for $D_1$ (cm) is $70 \leq D_1 \leq 500$, with $190 \leq D_1 \leq 400$ being yet more preferable.

If $L_1/D_1$ is less than 3 or greater than 30, then prolonged stable operation becomes difficult. A more preferable range for $L_1/D_1$ is $4 \leq L_1/D_1 \leq 20$, with $5 \leq L_1/D_1 \leq 15$ being yet more preferable.

If $n_1$ is less than 3, then the separation efficiency for the stripping section decreases and hence the desired separation efficiency cannot be attained. Moreover, to keep down the equipment cost while securing the desired separation efficiency, $n_1$ must be made to be not more than 30. Furthermore, if $n_1$ is greater than 30, then the pressure difference between the top and bottom of the column becomes too great, and hence prolonged stable operation becomes difficult, and moreover it becomes necessary to increase the temperature in the lower portion of the column, and hence side reactions become liable to occur. A more preferable range for $n_1$ is $5 \leq n_1 \leq 20$, with $6 \leq n_1 \leq 15$ being yet more preferable.

If $L_2$ (cm) is less than 1000, then the separation efficiency for the enrichment section decreases, and hence the desired separation efficiency cannot be attained. Moreover, to keep down the equipment cost while securing the desired separation efficiency, $L_2$ must be made to be not more than 5000. Furthermore, if $L_2$ is greater than 5000, then the pressure difference between the top and bottom of the column becomes too great, and hence prolonged stable operation becomes difficult. Moreover, it becomes necessary to increase the temperature in the lower portion of the column, and hence side reactions become liable to occur. A more preferable range for $L_2$ (cm) is $1500 \leq L_2 \leq 4000$, with $2000 \leq L_2 \leq 3500$ being yet more preferable.

If $D_2$ (cm) is less than 50, then it is not possible to attain the desired distillation amount. Moreover, to keep down the equipment cost while attaining the desired distillation amount, $D_2$ must be made to be not more than 500. A more preferable range for $D_2$ (cm) is $70 \leq D_2 \leq 400$, with $90 \leq D_2 \leq 350$ being yet more preferable.

If $L_2/D_2$ is less than 10 or greater than 50, then prolonged stable operation becomes difficult. A more preferable range for $L_2/D_2$ is $15 \leq L_2/D_2 \leq 40$, with $20 \leq L_2/D_2 \leq 35$ being yet more preferable.

If $n_2$ is less than 20, then the separation efficiency for the enrichment section decreases and hence the desired separation efficiency cannot be attained. Moreover, to keep down the equipment cost while securing the desired separation efficiency, $n_2$ must be made to be not more than 100. Furthermore, if $n_2$ is greater than 100, then the pressure difference between the top and bottom of the column becomes too great, and hence prolonged stable operation becomes difficult. Moreover, it becomes necessary to increase the temperature in the lower portion of the column, and hence side reactions become liable to occur. A more preferable range for $n_2$ is $30 \leq n_2 \leq 90$, with $40 \leq n_2 \leq 80$ being yet more preferable. Note that in the present invention, at least one chimney tray must be installed in the concentrating portion, and the number of stages therefor is included in $n_2$ above. Moreover, for the continuous multi-stage distillation column C of the present invention, preferably $D_2 \leq D_1$.

Furthermore, in the case that the high boiling point reaction mixture $A_B$ fed into the continuous multi-stage distillation column C contains a small amount of unreacted cyclic carbonate, it is preferable for it to be devised such that the unreacted cyclic carbonate is made to undergo reaction in a lower portion of the column, so that substantially no unreacted cyclic carbonate is contained in the column bottom component $C_B$. Accordingly, in a preferable embodiment of the present invention, a plurality ($n_3$ stages) of trays K are further provided in a lower portion of the internals in a lowermost portion of the stripping section which is in the lower portion of the continuous multi-stage distillation column C, some liquid are continuously withdrawn from an uppermost stage of the trays K, and given heat required for distillation and reaction in a reboiler, and then the heated liquid is returned into the distillation column C from a feeding port provided between the uppermost stage of the trays K and the internals in a lowermost portion of the enrichment section, while a remainder of the liquid is fed into lower trays in order.

By devising the continuous multi-stage distillation column C in this way, the residence time of liquid in the lower portion of the column can be increased. Moreover, by making a diameter $D_3$ of the column at and below the stages where the trays K are present be greater than the diameter $D_1$ of the enrichment section ($D_1 < D_3$), the amount of liquid held can be increased and hence the residence time can be increased, and thus a sufficient reaction time can be maintained. Furthermore, by making the column bottom liquid level be lower than the lowermost one of the trays K, back mixing of the liquid in the lower portion of the column can be prevented. As a result of the above, in the present invention, even in the case that a small amount of unreacted cyclic carbonate is contained, the unreacted cyclic carbonate can be reacted with the diol, which is generally present in a large excess, and thus converted completely into a dialkylene glycol having a high boiling point or the like.

The trays K may be any type of trays so long as these trays fulfill the role described above, but in terms of the relationship between performance and equipment cost, a sieve tray or a baffle trays is preferable, the baffle tray being particularly preferable. In the case of the sieve tray or the baffle tray, a weir is preferably provided, it preferably being made to be such that liquid overflowing the weir continuously falls down from a downcomer portion into lower stage trays. In this case, the weir height is preferably in a range of from 4 to 30 cm, more preferably from 6 to 20 cm, yet more preferably from 8 to 15 cm. In the case of the baffle tray, a simple tray in which the weir is the baffle is particularly preferable.

A preferable range for $D_3$ is $1.2D_1 < D_3 \leq 5D_1$, more preferably $1.5D_1 < D_3 \leq 4D_1$, yet more preferably $1.7D_1 < D_3 \leq 3D_1$.

Moreover, $n_3$ is not less than 2, a preferable range for $n_3$ being $3 \leq n_3 \leq 20$, more preferably $4 \leq n_3 \leq 15$, yet more preferably $5 \leq n_3 \leq 10$.

The chimney tray installed in the enrichment section of the continuous multi-stage distillation column C has provided therein at least one chimneys each having an opening having a cross-sectional area S ($cm^2$) in the plane of the tray. Moreover, a chimney cover is preferably installed on an upper opening of each of the chimneys. This chimney cover plays a role in a gaseous component that rises up from lower stages flowing sideways at the upper opening (gas outlet) of the chimney, and moreover plays a role in preventing a liquid component that falls down from upper stages from falling down directly into the lower stages.

The cross-sectional shape of each of the chimneys may be any of triangular, square, polygonal, circular, elliptical, star-shaped or the like, but a square shape or a circular shape is preferably used. Moreover, for each of the chimneys, the cross-sectional shape and area may vary from an upper portion to a lower portion of the chimney, but is preferably constant since then manufacture is simple and inexpensive. Moreover, the at least two chimneys may have different shapes to one another, but preferably have the same shape as one another.

In the present invention, the cross-sectional area S ($cm^2$) of the opening (the part of the chimney having the smallest cross section) of each of the chimneys connected to the chimney tray must satisfy the formula (10):

$$200 \leq S \leq 1000 \quad (10).$$

If S is less than 200, then a large number of chimneys are required to attain a predetermined production amount, and hence the equipment cost becomes high. If S is greater than 1000, then the flow of gas in the chimney tray stage is prone to becoming ununiform, and hence prolonged stable operation becomes difficult. A more preferable range for S ($cm^2$) is $300 \leq S \leq 800$, with $400 \leq S \leq 700$ being yet more preferable.

Moreover, the height h (cm) from the opening of each of the chimneys to the gas outlet (a lower end of the upper opening of the chimney) of that chimney must satisfy the formula (11):

$$10 \leq h \leq 80 \quad (11).$$

The chimney tray used in the present invention generally has installed therein a downcomer portion for allowing the liquid component to fall down into lower stages, and a weir for holding the liquid component. The height of the weir depends on h, but is generally set to approximately 5 to 20 cm less than h. Consequently, if h is less than 10, then the amount of liquid held in the chimney tray becomes low, and hence prolonged stable operation becomes difficult. Moreover, if h is greater than 80, then the amount of liquid held increases, and hence the strength of the equipment must be increased, and thus the equipment cost becomes high, and moreover the residence time of the purified diol in the column increases, which is undesirable. A more preferable range for h (cm) is $15 \leq h \leq 60$, with $20 \leq h \leq 50$ being yet more preferable.

An aperture ratio (the ratio of the total cross-sectional area of the openings in the chimneys to the area of the chimney tray including the total cross-sectional area of the openings) of the chimney tray is preferably in a range of from 10 to 40%. If the aperture ratio is less than 10%, then prolonged stable operation becomes difficult. Moreover, if the aperture ratio is greater than 40%, then the number of chimneys must be increased, or each of the chimneys must be made higher, and in either case the equipment cost becomes high. A more preferable range for the aperture ratio is 13 to 35%, with 15 to 30% being yet more preferable.

In the present invention, the at least one chimney tray is installed in the enrichment section (a portion above an inlet for feeding into the column but below the top of the column) of the multi-stage distillation column C, and a fraction having as a main component thereof intermediate boiling point material having a lower boiling point than that of the diol but a higher boiling point than that of the aliphatic monohydric alcohol is continuously withdrawn from the side cut outlet which is connected to the bottom of the liquid collecting portion of the chimney tray. The number of chimney trays can be made to be two or more if required, but is generally one. The stage at which the chimney tray is installed may be at any position in the enrichment section, but is preferably a stage that is at least 3 stages from the bottom of the stages in the enrichment section and at least 10 stages from the top of the stages in the enrichment section, more preferably a stage that is at least 4 stages from the bottom of the stages in the enrichment section and at least 15 stages from the top of the stages in the enrichment section, yet more preferably a stage that is at least 5 stages from the bottom of the stages in the enrichment section and at least 4 stages from the top of the stages in the enrichment section.

The continuous multi-stage distillation column C of the present invention preferably comprises a distillation column having trays and/or packings as internals in each of the stripping section and the enrichment section. The term "internal" used in the present invention means a part in the distillation column where gas and liquid are actually brought into contact with one another. Examples of the tray include a bubble-cap tray, a sieve tray, a ripple tray, a ballast tray, a valve tray, a counterflow tray, an Unifrax tray, a Superfrac tray, a Maxfrac tray, a dual flow tray, a grid plate tray, a turbogrid plate tray, a Kittel tray, or the like. Examples of the packing include random packings such as a Raschig ring, a Lessing ring, a Pall ring, a Berl saddle, an Intalox saddle, a Dixon packing, a McMahon packing or Heli-Pak, or structured packings such as Mellapak, Gempak, Techno-pack, Flexipac, a Sulzer packings, a Goodroll packing or Glitschgrid. A multi-stage distillation column having both a tray portion and a portion packed with packings can also be used. Furthermore, the term "number of stages $n_1$ or $n_2$ of the internal" used in the present invention means the number of trays in the case of trays, and the theoretical number of stages in the case of packings. $n_1$ or $n_2$ in the case of a continuous multi-stage distillation column having both a tray portion and a portion packed with packings is thus the sum of the number of trays and the theoretical number of stages.

In the present invention, the internals in the stripping section of the continuous multi-stage distillation column C and the internals excluding the chimney tray in the enrichment section are preferably trays and/or packings. Furthermore, it has been discovered that it is particularly preferable if the internals in the stripping section are trays, and the internals excluding the chimney tray in the enrichment section are trays and/or structured packings. Moreover, it has been discovered that sieve trays each having a sieve portion and a downcomer portion are particularly good as the trays in terms of the relationship between performance and equipment cost. It has also been discovered that each sieve tray preferably has 100 to 1000 holes/m$^2$ in the sieve portion thereof. A more preferable number of holes is from 150 to 900 holes/m$^2$, yet more preferably from 200 to 800 holes/m$^2$. Moreover, it has been discovered that the cross-sectional area per hole of each sieve tray is preferably in a range of from 0.5 to 5 cm$^2$. A more preferable cross-sectional area per hole is from 0.7 to 4 cm$^2$, yet more preferably from 0.9 to 3 cm$^2$. Furthermore, it has been discovered that it is particularly preferable if each sieve tray has 150 to 1200 holes/m in the sieve portion thereof, and the cross-sectional area per hole is in a range of from 0.5 to 5 cm$^2$.

An aperture ratio (the ratio of the total cross-sectional area of the holes in one tray stage to the area of the tray) of each of the sieve trays in the enrichment section of the continuous multi-stage distillation column C is preferably in a range of from 2 to 15%, more preferably from 2.5 to 12%, yet more preferably from 3 to 10%. Moreover, an aperture ratio (the ratio of the total cross-sectional area of the holes in one tray stage to the area of the tray) of each of the sieve trays in the enrichment section of the continuous multi-stage distillation column C is preferably in a range of from 1.5 to 12%, more preferably from 2 to 11%, yet more preferably from 2.5 to 10%. Note that in the present invention, the chimney tray installed in the enrichment section is counted in the number of stages, but as described above, the aperture ratio for the chimney tray is different to the aperture ratio for the sieve trays.

It has been shown that by adding the above conditions to the continuous multi-stage distillation column C, the object of the present invention can be attained more easily.

In the present invention, the dialkyl carbonate produced through the reactive distillation in the continuous multi-stage distillation column A is continuously withdrawn from the upper portion of the column in a gaseous form as the low boiling point reaction mixture $A_T$ together with aliphatic monohydric alcohol that has remained unreacted due to generally being used in excess. Moreover, the high boiling point reaction mixture $A_B$ containing the produced diol is continuously withdrawn from the lower portion of the column in a liquid form. The high boiling point reaction mixture $A_B$ having the diol as a main component thereof generally contains 10 to 45% by weight of residual aliphatic monohydric alcohol, a trace of the dialkyl carbonate, a very small amount (generally not more than 0.2% by weight) of unreacted cyclic carbonate, a small amount (generally not more than 0.4% by weight) of by-products having a lower boiling point than the diol (a 2-alkoxyethanol etc.), and a small amount (generally not more than 0.4% by weight) of by-products having a higher boiling point than the diol (e.g. a dialkylene glycol) including catalyst.

Material having a lower boiling point than that of the diol (the aliphatic monohydric alcohol, a trace of the dialkyl carbonate and by-produced $CO_2$, low boiling point by-products) and a small amount of the diol in the high boiling point reaction mixture $A_B$ continuously fed into the continuous multi-stage distillation column C are thus continuously withdrawn as the column top component $C_T$ and/or the side cut component $C_S$, while the diol containing the catalyst and a small amount of high boiling point by-products is continuously withdrawn as the column bottom component $C_B$. In the present invention, the concentration of the diol in the column bottom component $C_B$ is generally not less than 95% by weight, preferably not less than 97% by weight, more preferably not less than 98% by weight.

Moreover, in the process of the present invention, a very small amount (generally not more than 0.2% by weight) of unreacted cyclic carbonate fed into the continuous multi-stage distillation column C can be reacted with the diol, which is present in a large amount in the continuous multi-stage distillation column C, to produce a dialkylene glycol, and hence it is easy to make the amount of unreacted cyclic carbonate present substantially zero; in the present invention, the column bottom component $C_B$ generally having substantially no unreacted cyclic carbonate therein is continuously obtained.

Note that, generally, with an objective of obtaining an ultra high purity diol having a further reduced content of an aldehyde which may be contained in the diol in trace amount, or an ultra high purity diol having a high UV transmissivity, it is also preferable to feed a small amount of water into the lower portion of the continuous multi-stage distillation column C in accordance with the process described in Patent Document 9 (Japanese Patent Application Laid-Open No. 2002-308804) or Patent Document 10 (Japanese Patent Application Laid-Open No. 2004-131394).

The distillation conditions for the continuous multi-stage distillation column C used in the present invention vary depending on the form of the internals in the distillation column and the number of stages, the type, composition and amount of the high boiling point reaction mixture $A_B$ fed in, the purity of the diol required, and so on. The column bottom temperature is generally preferably a specified temperature in a range of from 150 to 250° C. A more preferable column bottom temperature range is from 170 to 230° C., yet more preferably from 190 to 210° C. The column bottom pressure varies depending on the composition in the column and the column bottom temperature used, but is generally in a range of from 50000 to 300000 Pa, preferably from 80000 to 250000 Pa, more preferably from 100000 to 200000 Pa.

Moreover, the reflux ratio for the continuous multi-stage distillation column C is preferably in a range of from 0.3 to 5, more preferably from 0.5 to 3, yet more preferably from 0.8 to 2.

In the present invention, the content of the diol in the column top component $C_T$ from the continuous multi-stage distillation column C is generally not more than 100 ppm, preferably not more than 50 ppm, more preferably not more than 10 ppm, yet more preferably not more than 5 ppm. In the present invention, it is even possible to make the content of the diol in the column top component $C_T$ be zero.

The side cut component $C_S$ from the continuous multi-stage distillation column C generally contains the aliphatic monohydric alcohol, by-products having a lower boiling point than that of the diol (a 2-alkoxyethanol etc.), the diol, and a small amount of impurities having a higher boiling point than that of the diol (e.g. a dialkylene glycol). The amount of the side cut component $C_S$ is generally not more than 4%, preferably not more than 3%, more preferably not more than 2%, of the high boiling point reaction mixture $A_B$ fed into the continuous multi-stage distillation column C.

Moreover, in the present invention, the content of the diol in the side cut component $C_S$ can generally easily be made to be not more than 0.5%, preferably not more than 0.4%, more preferably not more than 0.3%, of the diol fed into the continuous multi-stage distillation column C.

As the column bottom component $C_B$ from the continuous multi-stage distillation column C, the diol can be continuously obtained containing generally not more than 2%, preferably not more than 1.5%, more preferably not more than 1%, of by-products having a higher boiling point than that of the diol (e.g. a dialkylene glycol) and a small amount of catalyst component. The diol obtained as the column bottom component $C_B$ is generally not less than 99.5%, preferably not less than 99.6%, more preferably not less than 99.7%, of the diol fed into the continuous multi-stage distillation column C. It is a characteristic feature of the present invention that the diol can be obtained with such a high recovery.

Moreover, in a preferable embodiment of the present invention, the reaction is carried out using starting materials and a catalyst not containing a halogen, and hence the produced diol can be made to not contain a halogen at all. In the present invention, a diol having a halogen content of not more than 0.1 ppm, preferably not more than 1 ppb, can thus be easily produced.

In the present invention, the reaction yield and the purification yield are thus high, and hence the diol can be produced with a high yield of generally not less than 97%, preferably not less than 98%, more preferably not less than 99%, based on the cyclic carbonate used.

The material constituting each of the continuous multi-stage distillation columns A and C which are used in the present invention is generally a metallic material such as carbon steel or stainless steel. In terms of the quality of the dialkyl carbonate and diol to be produced, stainless steel is preferable.

EXAMPLES

Following is a more detailed description of the present invention through examples. However, the present invention is not limited to the following examples. Note that the halogen content was measured using ion chromatography.

Example 1

A continuous multi-stage distillation column C as shown in FIG. 1 having $L_1$=1100 cm, $D_1$=110 cm, $L_1/D_1$=10, $n_1$=10, $L_2$=3000 cm, $D_2$=110 cm, $L_2/D_2$=27.3, and $n_2$=60 was used. The inside diameter ($D_3$) was increased to 200 cm over approximately 500 cm from the bottom of the column, and in this portion there were installed 8 stages of baffle trays K having a downcomer portion and for which a weir (height 10 cm) was the baffle. It was devised such that some liquid was continuously withdrawn from a lower portion of the uppermost stage of the baffle trays K, the withdrawn liquid being heated by a reboiler, and then fed back into an upper portion of this stage. Moreover, in the enrichment section, an upper portion was packed with Mellapak with a theoretical number of stages of 52, one chimney tray stage was installed below the Mellapak, and 8 stages of trays were provided below the chimney tray. In this example, sieve trays were used as the internals in the stripping section, and sieve trays were used as the trays in the enrichment section. These sieve trays had a cross-sectional area per hole of approximately 1.3 cm$^2$. In the stripping section, the number of holes in each of the sieve trays was approximately 250 to 300/m$^2$, and the aperture ratio was in a range of from 3 to 4%. Moreover, in the enrichment section, the number of holes in each of the sieve trays was approximately 150 to 300/m$^2$, and the aperture ratio was in a range of from 2.8 to 3.6%. The chimney tray had four chimneys therein, each of the chimneys having S=approximately 500 cm$^2$ and h=25 cm, and the aperture ratio being in a range of from 18 to 25%. The chimney tray had a downcomer portion, the weir height being 10 cm.

A starting material containing ethylene carbonate (EC) and methanol (MeOH) (molar ratio MeOH/EC=8.4) and a catalyst (KOH in ethylene glycol subjected to thermal dehydration treatment; K concentration 0.1% by weight based on EC) was continuously fed into a continuous multi-stage distillation column A, and reactive distillation was carried out, whereby 3.205 ton/hr of a column bottom component $A_B$ was continuously withdrawn. The ethylene carbonate conversion was 100%, and the ethylene glycol selectivity was 99.8%. The column bottom component $A_B$, which contained 0.99 ton/hr of methanol, 0.001 ton/hr of dimethyl carbonate, 0.009 ton/hr of 2-methoxyethanol, 2.186 ton/hr of ethylene glycol, and 0.019 ton/hr of diethylene glycol and catalyst component, was continuously fed into a continuous multi-stage distillation column C from an inlet. This inlet was installed between the trays in the $10^{th}$ and $11^{th}$ stages from the bottom of the continuous multi-stage distillation column C.

The continuous multi-stage distillation column C was operated continuously with a column bottom temperature of approximately 200° C., a column top pressure of approximately 11000 Pa, and a reflux ratio of 0.9. Moreover, the column bottom liquid level was kept below the lowermost one of the trays K.

It was possible to attain stable steady state operation after 24 hours.

A column top component $C_T$ containing 0.968 ton/hr of methanol, and 0.001 ton/hr of dimethyl carbonate, a side cut component $C_S$ containing 0.022 ton/hr of methanol, 0.009 ton/hr of 2-methoxyethanol, and 0.004 ton/hr of ethylene glycol, and a column bottom component $C_B$ containing 2.182 ton/hr of ethylene glycol, and 0.019 ton/hr of diethylene glycol, catalyst component and high boiling point by-products were continuously withdrawn from the continuous multi-stage distillation column C.

The content of ethylene glycol in the column top component $C_T$ was not more than 5 ppm, i.e. substantially zero. Moreover, the content of ethylene glycol in the side cut component $C_S$ was 0.18% of the ethylene glycol fed into the continuous multi-stage distillation column C.

The concentration of ethylene glycol in the column bottom component $C_B$ was 99.1% by weight. Moreover, 99.82% of the ethylene glycol fed into the continuous multi-stage distillation column C was recovered as the column bottom component $C_B$. The ethylene glycol yield based on the ethylene carbonate was 99.6%.

Prolonged continuous operation was carried out under these conditions. After 500 hours, 2000 hours, 4000 hours, 5000 hours, and 6000 hours, the produced amounts of ethylene glycol per hour were 2.182 ton, 2.182 ton, 2.182 ton, 2.182 ton, and 2.182 ton, and hence operation was very stable.

Example 2

A starting material containing ethylene carbonate (3.565 ton/hr) and methanol (molar ratio MeOH/EC=8) and a catalyst (KOH in ethylene glycol subjected to thermal dehydration treatment; K concentration 0.1% by weight based on EC) was continuously fed into a continuous multi-stage distillation column A, and reactive distillation was carried out, whereby dimethyl carbonate and ethylene glycol were produced with similar reaction results to in Example 1, a column bottom component $A_B$ having ethylene glycol as a main component thereof being continuously withdrawn. The ethylene glycol was separated out by distillation using the same continuous multi-stage distillation column C as in Example 1 and a similar process.

It was possible to attain stable steady state operation after 24 hours.

The column bottom component $C_B$, which was continuously withdrawn from the continuous multi-stage distillation column C at 2.472 ton/hr, contained 2.439 ton/hr of ethylene glycol, and 0.033 ton/hr of diethylene glycol, catalyst component and high boiling point by-products. The concentration of ethylene glycol in the column bottom component $C_B$ was 99.1% by weight. Moreover, 99.8% of the ethylene glycol fed into the continuous multi-stage distillation column C was recovered as the column bottom component $C_B$. The ethylene glycol yield based on the ethylene carbonate was 99.5%.

Prolonged continuous operation was carried out under these conditions. After 1000 hours, 2000 hours, 3000 hours, and 5000 hours, the produced amounts of ethylene glycol per hour were 2.439 ton, 2.439 ton, 2.439 ton, and 2.439 ton, and hence operation was very stable.

Example 3

A continuous multi-stage distillation column C very similar to that used in Example 1 was used. However, the number of holes in each of the sieve trays in the stripping section and the enrichment section was approximately 550 to 650/m$^2$, and the aperture ratio was in a range of from 6.5 to 8.5%.

A starting material containing ethylene carbonate (8.20 ton/hr) and methanol (molar ratio MeOH/EC=9) and a catalyst (KOH in ethylene glycol subjected to thermal dehydration treatment; K concentration 0.1% by weight based on EC) was continuously fed into a continuous multi-stage distillation column A, and reactive distillation was carried out, whereby dimethyl carbonate and ethylene glycol were produced with similar reaction results to in Example 1, a column bottom component $A_B$ having ethylene glycol as a main component thereof being continuously withdrawn. The ethylene glycol was separated out by distillation using the continuous multi-stage distillation column C and a similar process to Example 1.

It was possible to attain stable steady state operation after 24 hours.

The column bottom component $C_B$, which was continuously withdrawn from the continuous multi-stage distillation column C at 5.852 ton/hr, contained 5.754 ton/hr of ethylene glycol, and 0.098 ton/hr of diethylene glycol, catalyst component and high boiling point by-products. The concentration of ethylene glycol in the column bottom component $C_B$ was 98.3% by weight. Moreover, 99.8% of the ethylene glycol fed into the continuous multi-stage distillation column C was recovered as the column bottom component $C_B$. The ethylene glycol yield based on the ethylene carbonate was 99.6%.

Prolonged continuous operation was carried out under these conditions. After 500 hours, 1000 hours, and 1500 hours, the produced amounts of ethylene glycol per hour were 5.754 ton, 5.754 ton, and 5.754 ton, and hence operation was very stable.

INDUSTRIAL APPLICABILITY

According to the present invention, there are provided a specific industrial apparatus and industrial production process that are inexpensive and enable a diol to be produced in an amount of not less than 1 ton/hr, preferably not less than 2 tons/hr, more preferably 3 tons/hr, stably for a prolonged period of time (e.g. not less than 1000 hours, preferably not less than 3000 hours, more preferably not less than 5000 hours) by taking a cyclic carbonate and an aliphatic monohydric alcohol as starting materials, continuously feeding the starting materials into a continuous multi-stage distillation column A in which a catalyst is present, carrying out reactive distillation in the column A, continuously withdrawing a low boiling point reaction mixture $A_T$ containing a produced dialkyl carbonate and the aliphatic monohydric alcohol from an upper portion of the column A in a gaseous form, continuously withdrawing a high boiling point reaction mixture $A_B$ containing a produced diol from a lower portion of the column A in a liquid form, then continuously feeding the high boiling point reaction mixture $A_B$ into a continuous multi-stage distillation column C for separating off material having a lower boiling point than that of the diol contained in the high boiling point reaction mixture $A_B$, continuously obtaining the material having a lower boiling point than that of the diol as a column top component $C_T$ and a side cut component $C_S$, and continuously obtaining the diol substantially not containing the material having a lower boiling point than that of the diol as a column bottom component $C_B$. The present invention is thus very useful industrially.

We claim:

1. In an industrial process for the production of a diol in which a diol is produced by taking a cyclic carbonate and an aliphatic monohydric alcohol as starting materials, continuously feeding the starting materials into a continuous multi-stage distillation column A in which a catalyst is present, carrying out reactive distillation in said column A, continuously withdrawing a low boiling point reaction mixture $A_T$ containing a produced dialkyl carbonate and said aliphatic monohydric alcohol from an upper portion of the column A in a gaseous form, continuously withdrawing a high boiling point reaction mixture $A_B$ containing a produced diol from a lower portion of the column A in a liquid form, then continuously feeding said high boiling point reaction mixture $A_B$ into a continuous multi-stage distillation column C for separating off material having a lower boiling point than that of the diol contained in said high boiling point reaction mixture $A_B$, continuously obtaining the material having a lower boiling point than the diol as a column top component $C_T$ and a side cut component $C_S$, and continuously obtaining the diol substantially not containing the material having a lower boiling point than that of the diol as a column bottom component $C_B$, wherein the improvement comprises:

(a) said continuous multi-stage distillation column C comprises a continuous multi-stage distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1, D_1, n_1, L_2, D_2$, and $n_2$ satisfy the following formulae (1) to (9):

$$300 \leq L_1 \leq 3000 \quad (1)$$

$$50 \leq D_1 \leq 700 \quad (2)$$

$$3 \leq L_1/D_1 \leq 30 \quad (3)$$

$$3 \leq n_1 \leq 30 \quad (4)$$

$$1000 \leq L_2 \leq 5000 \quad (5)$$

$$50 \leq D_2 \leq 500 \quad (6)$$

$$10 \leq L_2/D_2 \leq 50 \quad (7)$$

$$20 \leq n_2 \leq 100 \quad (8) \text{ and}$$

$$D_2 \leq D_1 \quad (9);$$

(b) the enrichment section of said continuous multi-stage distillation column C has at least one chimney tray installed therein as an internal, said chimney tray having installed therein one or more chimneys each having an opening having a cross-sectional area S (cm$^2$) satisfying the formula (10):

$$200 \leq S \leq 1000 \quad (10),$$

and each of the chimneys being such that a height h (cm) from said opening of said chimney to a gas outlet of said chimney satisfies the formula (11):

$$10 \leq h \leq 80 \quad (11); \text{ and}$$

(c) a side cut outlet is connected to a liquid collecting portion of said chimney tray of said continuous multi-stage distillation column C.

2. The process according to claim 1, wherein an amount produced of the diol is not less than 1 ton/hr.

3. The process according to claim 1, wherein a plurality ($n_3$ stages) of trays K are further provided in a lower portion of the internals in a lowermost portion of the stripping section which is in a lower portion of said continuous multi-stage distillation column C, a liquid is continuously withdrawn from an uppermost stage of said trays K, and after heat is given to require for distillation in a reboiler, the heated liquid is returned into the distillation column C from a feeding port provided between the uppermost stage of the trays K and the internal in the lowermost portion of the stripping section, while a remainder of the liquid is fed into a lower tray in order.

4. The process according to claim 3, wherein each of the trays K is a baffle tray.

5. The process according to claim 3, wherein an inside diameter $D_3$ of said continuous multi-stage distillation column C where the trays K are present satisfies $D_1 \leq D_3$.

6. The process according to claim 3, wherein $L_1, D_1, L_1/D_1, n_1, L_2, D_2, L_2/D_2, n_2$, and $n_3$ for said continuous multi-stage distillation column C satisfy respectively $500 \leq L_1 \leq 2000$, $70 \leq D_1 \leq 500$, $5 \leq L_1/D_1 \leq 20$, $5 \leq n_1 \leq 20$, $1500 \leq L_2 \leq 4000$, $70 \leq D_2 \leq 400$, $15 \leq L_2/D_2 \leq 40$, $30 \leq n_2 \leq 90$, and $3 \leq n_3 \leq 20$.

7. The process according to claim 1, wherein the internal in the stripping section of said continuous multi-stage distillation column C and the internal excluding the chimney tray in the enrichment section are trays and/or packings.

8. The process according to claim 7, wherein the internal in the stripping section of said continuous multi-stage distillation column C is the tray, and the internal excluding the chimney tray in the enrichment section are trays and/or structured packings.

9. The process according to claim 7, wherein said tray is a sieve tray.

10. The process according to claim 9, wherein said sieve tray has 100 to 1000 holes/m$^2$ in a sieve portion thereof, and a cross-sectional area per hole in a range of from 0.5 to 5 cm$^2$.

11. The process according to claim 9, wherein an aperture ratio (a ratio of a total cross-sectional area of the hole in one tray stage to an area of the tray) of said sieve tray in the enrichment section of said continuous multi-stage distillation column C is in a range of from 2 to 15%.

12. The process according to claim 9, wherein an aperture ratio (a ratio of a total cross-sectional area of the hole in one tray stage to an area of the tray) of said sieve tray in the enrichment section of said continuous multi-stage distillation column C is in a range of from 1.5 to 12%.

13. The process according to claim 1, wherein an aperture ratio (a ratio of a total cross-sectional area of the opening in the chimney to an area of the chimney tray including a total cross-sectional area of the opening) of said chimney tray is in a range of from 10 to 40%.

14. The process according to claim 1, wherein said continuous multi-stage distillation column C has a column bottom temperature in a range of from 150 to 250° C.

15. The process according to claim 1, wherein said continuous multi-stage distillation column C has a column top pressure in a range of from 50000 to 300000 Pa.

16. The process according to claim 1, wherein said continuous multi-stage distillation column C has a reflux ratio in a range of from 0.3 to 5.

17. The process according to claim 1, wherein a content of the diol in said column top component $C_T$ is not more than 100 ppm.

18. The process according to claim 1, wherein a content of the diol in said side cut component $C_S$ is not more than 0.5% of the diol fed into said continuous multi-stage distillation column C.

19. A continuous multi-stage distillation column being a continuous multi-stage distillation column C for producing a diol, wherein:

(a) said continuous multi-stage distillation column C comprises a distillation column comprising a stripping section having a length $L_1$ (cm), an inside diameter $D_1$ (cm) and an internal with a number of stages $n_1$ thereinside, and an enrichment section having a length $L_2$ (cm), an inside diameter $D_2$ (cm) and an internal with a number of stages $n_2$ thereinside, wherein $L_1$, $D_1$, $n_1$, $L_2$, $D_2$, and $n_2$ satisfy the following formulae (1) to (9):

$$300 \leq L_1 \leq 3000 \tag{1}$$

$$50 \leq D_1 \leq 700 \tag{2}$$

$$3 \leq L_1/D_1 \leq 30 \tag{3}$$

$$3 \leq n_1 \leq 30 \tag{4}$$

$$1000 \leq L_2 \leq 5000 \tag{5}$$

$$50 \leq D_2 \leq 500 \tag{6}$$

$$10 \leq L_2/D_2 \leq 50 \tag{7}$$

$$20 \leq n_2 \leq 100 \tag{8} \text{ and}$$

$$D_2 \leq D_1 \tag{9};$$

(b) the enrichment section of said continuous multi-stage distillation column C has at least one chimney tray installed therein as an internal, the chimney tray having installed therein one or more chimneys each having an opening having a cross-sectional area S (cm$^2$) satisfying the formula (10):

$$200 \leq S \leq 1000 \tag{10},$$

and each of the chimneys being such that a height h (cm) from said opening of said chimney to a gas outlet of the chimney satisfies the formula (II):

$$10 \leq h \leq 80 \tag{11}; \text{ and}$$

(c) a side cut outlet is connected to a liquid collecting portion of said chimney tray of said continuous multi-stage distillation column C.

20. The continuous multi-stage distillation column according to claim 19, wherein a plurality ($n_3$ stages) of trays K are further provided in a lower portion of the internals in a lowermost portion of the stripping section which is in a lower portion of said continuous multi-stage distillation column C.

21. The continuous multi-stage distillation column according to claim 20, wherein each of the trays K is a baffle tray.

22. The continuous multi-stage distillation column according to claim 20, wherein an inside diameter $D_3$ of said column where the trays K are present satisfies $D_1 \leq D_3$.

23. The continuous multi-stage distillation column according to claim 19, wherein $L_1$, $D_1$, $L_1/D_1$, $n_1$, $L_2$, $D_2$, $L_2/D_2$, $n_2$, and $n_3$ satisfy respectively $500 \leq L_1 \leq 2000$, $70 \leq D_1 \leq 500$, $5 \leq L_1/D_1 \leq 20$, $5 \leq n_1 \leq 20$, $1500 \leq L_2 \leq 4000$, $70 \leq D_2 \leq 400$, $15 \leq L_2/D_2 \leq 40$, $30 \leq n_2 \leq 90$, and $3 \leq n_3 \leq 20$.

24. The continuous multi-stage distillation column according to claim 19, wherein the internal in the stripping section of the stripping section and the internal excluding the chimney tray in the enrichment section are trays and/or packings.

25. The continuous multi-stage distillation column according to claim 24, wherein the internal in the stripping section is a tray, and the internal excluding the chimney tray in the enrichment section is a tray and/or a structured packing.

26. The continuous multi-stage distillation column according to claim 24, wherein said tray is a sieve tray.

27. The continuous multi-stage distillation column according to claim 26, wherein said sieve tray has 100 to 1000 holes/m$^2$ in a sieve portion thereof, and a cross-sectional area per hole in a range of from 0.5 to 5 cm$^2$.

28. The continuous multi-stage distillation column according to claim 26, wherein an aperture ratio (a ratio of a total cross-sectional area of the hole in one tray stage to an area of the tray) of said sieve tray in the stripping section is in a range of from 2 to 15%.

29. The continuous multi-stage distillation column according to claim 26, wherein an aperture ratio (a ratio of a total cross-sectional area of the hole in one tray stage to an area of the tray) of said sieve trays in the enrichment section is in a range of from 1.5 to 12%.

30. The continuous multi-stage distillation column according to claim 19, wherein an aperture ratio (a ratio of a total cross-sectional area of the opening in the chimneys to an area of the chimney tray including a total cross-sectional area of the opening) of said chimney tray is in a range of from 10 to 40%.

* * * * *